United States Patent
Li et al.

(10) Patent No.: US 8,455,532 B2
(45) Date of Patent: Jun. 4, 2013

(54) PYRAZOLYL ACRYLONITRILE COMPOUNDS AND USES THEREOF

(75) Inventors: Bin Li, Shenyang (CN); Haibo Yu, Shenyang (CN); Hong Zhang, Shenyang (CN); Yan Cheng, Shenyang (CN); Yanmei Luo, Shenyang (CN); Lizeng Wang, Beijing (CN); Hongfei Wu, Beijing (CN); Man Xu, Beijing (CN)

(73) Assignees: Shenyang Research Institute of Chemical Industry Co., Ltd., Liaoning (CN); Sinochem Corporation, Beijing ( * ) Notice: Subject to any disclaimer, the term of this patent is extended or adjusted under 35 U.S.C. 154(b) by 38 days.

(21) Appl. No.: 13/265,010

(22) PCT Filed: Apr. 27, 2010

(86) PCT No.: PCT/CN2010/072224
§ 371 (c)(1),
(2), (4) Date: Oct. 18, 2011

(87) PCT Pub. No.: WO2010/124617
PCT Pub. Date: Nov. 4, 2010

(65) Prior Publication Data
US 2012/0035236 A1    Feb. 9, 2012

(30) Foreign Application Priority Data
Apr. 29, 2009   (CN) .......................... 2009 1 0083205

(51) Int. Cl.
*A01N 43/56* (2006.01)
*C07D 231/12* (2006.01)

(52) U.S. Cl.
USPC ...................................... 514/406; 548/375.1

(58) Field of Classification Search
None
See application file for complete search history.

(56) References Cited

FOREIGN PATENT DOCUMENTS

| | | | |
|---|---|---|---|
| CN | 101367784 A | | 2/2009 |
| JP | 2000119256 | * | 4/2000 |
| JP | 2003201280 A | | 7/2003 |
| WO | 9740009 A | | 10/1997 |

OTHER PUBLICATIONS

International Search Report Received in PCT/CN2010/072224, mailed Jul. 29, 2010. English translation provided.

* cited by examiner

*Primary Examiner* — Kamal Saeed
(74) *Attorney, Agent, or Firm* — Smith, Gambrell & Russell, LLP

(57) ABSTRACT

A kind of pyrazolyl acrylniitrile compounds represented by the structures of formula I or stereoisomers thereof are disclosed in the present invention.

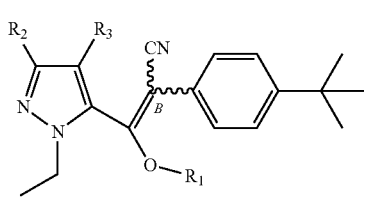

Figure 1:
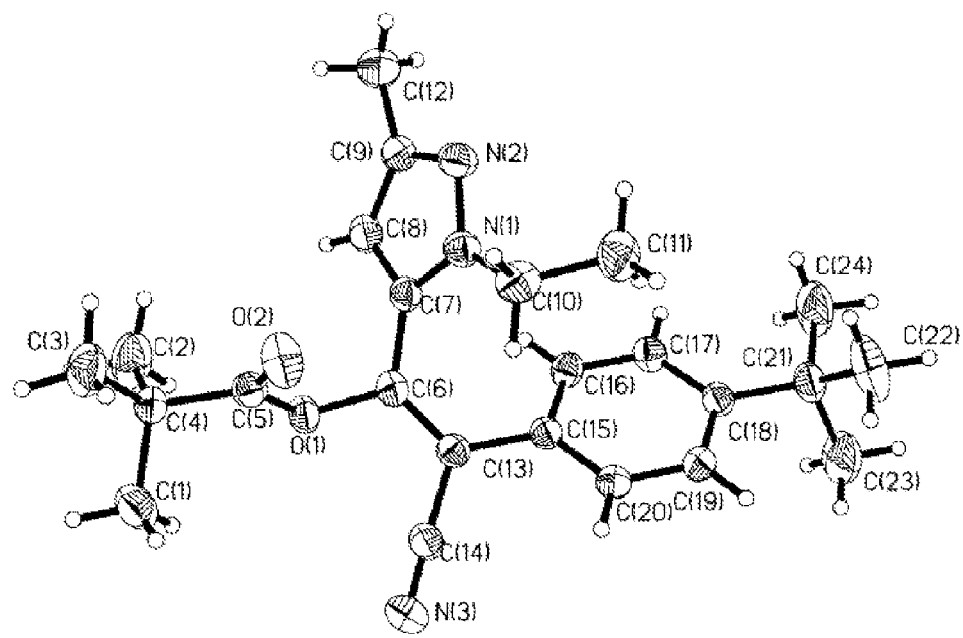

Where in: $R_1$ is selected from the group of substituents consisting of H, $C_1$-$C_4$ alkoxy $C_1$-$C_2$ alkyl, $C_3$-$C_5$ alkenyloxy $C_1$-$C_2$ alkyl, $C_3$-$C_5$ alknyloxy $C_1$-$C_2$ alkyl, $C_1$-$C_4$ alkylthio $C_1$-$C_2$ alkyl, $C_1$-$C_5$ alkyl carbonyl, $C_3$-$C_8$ cycloalkyl carbonyl, $C_1$-$C_5$ alkoxy carbonyl or $C_1$-$C_5$ alkylthio carbonyl; $R_2$ is Cl or methyl; $R_3$ is H, methyl, CN, $NO_2$ or halogen. Or its stereoisomers.

The Formula I compounds have high insecticidal activities or acaricidal activities, so they can be used as insecticide or acaricide.

6 Claims, 3 Drawing Sheets

PYRAZOLYL ACRYLONITRILE COMPOUNDS AND USES THEREOF

FIELD OF THE INVENTION

The present invention relates to insecticide or acaricide, specifically to a kind of pyrazolyl acrylonitrile compounds and uses thereof.

BACKGROUND OF THE INVENTION

Since insect pests or mite will become resistant to insecticides or acaricides used for a period of time, it is necessary to invent continuously new compounds and compositions with improved insecticidal and/or acaricidal activity. Simultaneously, with the growing demands for agricultural and animal products, as well as the awareness on the environmental protection, the cost-effective or environmentally friendly novel insecticides or acaricides are always in demand.

Some 1-methylpyrazolyl acrylonitrile compounds and uses thereof were disclosed in CN1763003A, JP2003201280A, JP2003206281A and CN101367784A. The compound $KC_1$ showed good insecticidal and acaricidal activity in JP2003206280A. It has been commercialized as a acaricide with the common name of cyenopyrafen, whose stereoisomer compound $KC_2$ was also disclosed. The compound $KC_3$ showed more than 80% mortality against spider mite at 400 ppm in CN101367784A.

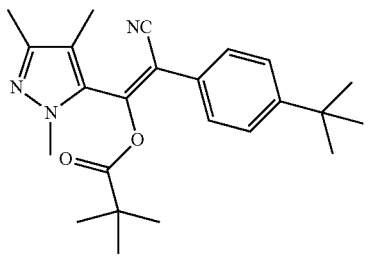

$KC_1$ (cyenopyrafen, E configration)

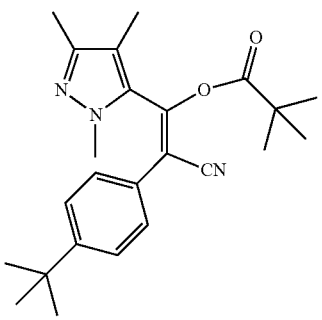

$KC_2$ (Z configration)

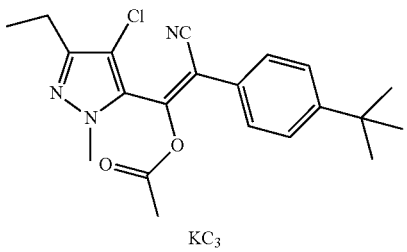

$KC_3$

Neither the preparation of 2-phenyl or substituted phenyl-3-(1-ethyl pyrazolyl) acrylonitrile compounds, nor their insecticidal or acaricidal activities is described in state of the arts.

SUMMARY OF THE INVENTION

The purpose of the present invention is to provide a kind of novel pyrazolyl acrylonitrile compounds, and their applications for controlling insects or mites in agriculture, forestry or public health.

Detailed description of this invention is as follows:

The present invention provides a kind of pyrazolyl acrylonitrile compounds as represented by the general formula I:

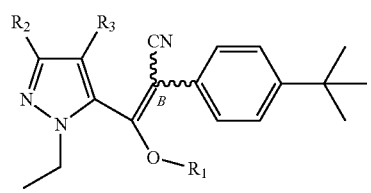

I

Wherein:

$R_1$ is selected from H, $C_1$-$C_4$ alkoxy $C_1$-$C_2$ alkyl, $C_3$-$C_5$ alkenyloxy $C_1$-$C_2$ alkyl, $C_3$-$C_5$ alkynyloxy $C_1$-$C_2$ alkyl, $C_1$-$C_4$ alkylthio $C_1$-$C_2$ alkyl, $C_1$-$C_5$ alkyl carbonyl, $C_3$-$C_8$ cycloalkyl carbonyl, $C_1$-$C_5$ alkoxy carbonyl or $C_1$-$C_5$ alkylthio carbonyl;

$R_2$ is selected from Cl or methyl;

$R_3$ is selected from H, methyl, CN, $NO_2$ or halogen;

Or its stereoisomers.

The preferred compounds of the general formula I in the present invention are:

$R_1$ is selected from H, $C_1$-$C_4$ alkoxy $C_1$-$C_2$ alkyl, $C_1$-$C_5$ alkyl carbonyl, $C_3$-$C_8$ cycloalkyl carbonyl or $C_1$-$C_5$ alkoxy carbonyl;

$R_2$ is methyl;

$R_3$ is selected from H, methyl, CN or halogen;

Or its stereoisomers.

Taking the convenient synthesis, preparation cost, environmentally friendliness and other factors into account the more preferred compounds of the general formula I in the invention are:

$R_1$ is selected from $C_1$-$C_2$ alkoxy methyl, $C_4$-$C_5$ alkyl carbonyl, $C_3$-$C_5$ cycloalkyl carbonyl or $C_1$-$C_2$ alkoxy carbonyl;

$R_2$ is methyl;

$R_3$ is selected from H, CN, F or Cl;

Or its stereoisomers.

In above definitions of the compounds of general formula I, the term "alkyl" indicates straight-chain or branched alkyl such as methyl, ethyl, n-propyl, i-propyl, n-butyl, i-butyl, s-butyl, t-butyl, 2-methyl-butyl, n-pentyl, i-pentyl etc. "Cycloalkyl" indicates cyclo-chain forms such as cyclopropyl, 1-methylcyclopropyl, 1,2-di-methylcyclopropyl, 1,2,3-tri-methylcyclopropyl 1,2,2,3-tetra-methylcyclopropyl, 1,2,2,3,3-penta-methylcyclopropyl, cyclobutyl, cyclopentyl and cyclohexyl, etc. "Alkenyl" indicates straight-chain or branched alkenes such as 1-propenyl, 2-propenyl, 1-butenyl 2-butenyl, 3-butenyl, 1-pentenyl, 2-pentenyl, 3-pentenyl and 4-pentenyl. "Alkynyl" includes straight-chain or branched alkynes such as 1-propynyl, 2-propynyl, 1-butynyl, 2-butynyl, 3-butynyl, 1-pentynyl, 2-pentynyl, 3-pentynyl and 4-pentynyl. "Alkoxy" is that the end of alkyl is oxygen, such as methoxy, ethoxy, n-propyloxy, i-propyloxy and t-butoxy, etc. "Alkylthio" is that the end of alkyl is sulfur, such as methylthio, ethylthio, n-propylthio, i-propylthio, t-butylthio, etc. "Halogen" is fluorine, chlorine, bromine, iodine. Stereoisomers referred to E- and Z-isomer in general formula I. When the substitutes CN and $OR_1$ are at same side in double bond B, the configuration is Z form. When the substituents CN and $OR_1$ are at different side in double bond B, the configuration is E form.

The compounds of general formula I in the present invention can be prepared by the following methods, unless further specification, the substituents in the reaction schemes are the same as above definitions:

When $R_1$ is hydrogen, the compounds of general formula I in the present invention can be prepared by the following method:

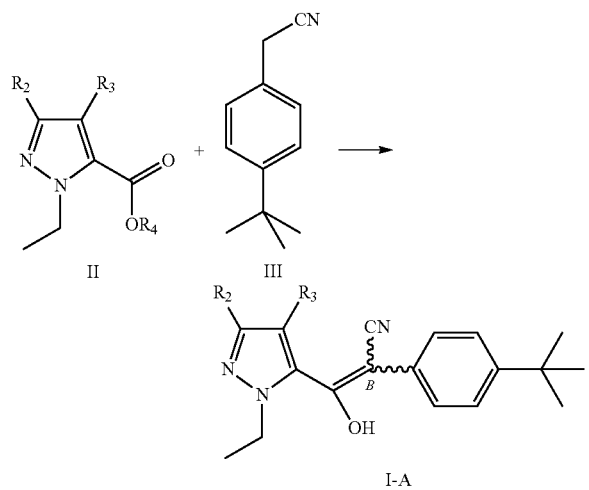

The compounds of general formula II (The compounds can be prepared according to the procedures disclosed in the JP2001342178A and CN1626520A. $R_4$ is selected from $C_1$-$C_4$ alkyl) and III (The compounds can be prepared according to the procedures disclosed in the *Organic Syntheses*, Coll. 1941, 1, 107 and *Organic Syntheses*, Coll. 1922, 2, 9) are reacted in appropriate solvent to yield the compounds of general formula I-A at a certain temperature from −10° C. to boiling point for 30 minutes to 48 hours with the presence of base.

The appropriate solvent is selected from dichloromethane, chloroform, carbon tetrachloride, benzene, toluene, methanol, ethanol, ethyl acetate, acetonitrile, tetrahydrofuran, dioxane, N,N-dimethylformamide, dimethyl sulfoxide, 2-methylpentane, methyl-cyclopentane, hexane, cyclohexane, methylcyclohexane, heptane, octane, decane, butyl ether, ethylene glycol dimethyl ether, ethylene glycol diethyl ether, ethylene glycol dibutyl ether, ethylene glycol methyl ether, ethylene glycol ethyl ether, ethylene glycol butyl ether, etc., or the mixture of two or three above solvents.

The addition of appropriate base is advantageous to the reaction. The appropriate base is selected from organic base such as triethylamine, N,N-dimethylaniline, pyridine, 2-methyl-pyridine, 3-methylpyridine, 4-methylpyridine, 5-ethyl-2-methylpyridine, 2,3-dimethylpyridine, 2,4-dimethylpyridine, 3,5-dimethylpyridine, 2,6-dimethylpyridine, 2,4,6-trimethylpyridine, quinoline, sodium methoxide, sodium ethoxide, sodium tert-butoxide or potassium tert-butoxide etc., or inorganic base such as sodium hydroxide, potassium hydroxide, sodium carbonate or potassium carbonate etc.

When $R_1$ is other than hydrogen, the compounds of general formula I in the present invention can be prepared by the following method:

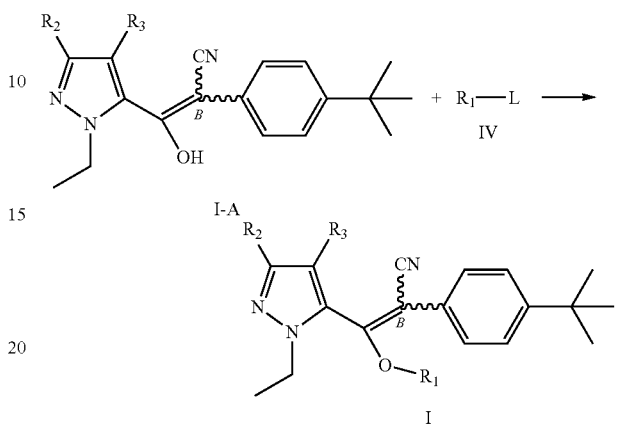

L stands for appropriate leave group, such as chlorine atom, broine atom or p-toluenesulfonate, etc.

The compounds of general formula I-A and IV (such as halogenated alkyl, sulfonate and acyl halogen, which can be prepared according to the procedures disclosed in the *Synthesis*, (11), 942-4; 1982 and *Journal of Medicinal Chemistry*, 29(5), 849-52; 1986) are reacted in appropriate solvent to yield the compounds of general formula I at a certain temperature from −10° C. to boiling point for 30 minutes to 48 hours.

The appropriate solvent is selected from tetrahydrofuran, dichloromethane, chloroform, carbon tetrachloride, hexane, benzene, toluene, ethyl acetate, acetonitrile, dioxane, N,N-dimethylformamide and dimethyl sulfoxide etc.

The addition of appropriate base is advantageous to the reaction. The appropriate base is selected from organic base such as triethylamine, N,N-dimethylaniline, pyridine, sodium methoxide, sodium ethoxide, sodium tert-butoxide or potassium tert-butoxide etc., or inorganic base such as sodium hydroxide, potassium hydroxide, sodium carbonate or potassium carbonate etc.

In compounds of general formula I having double bond B, stereoisomers referred to as Z isomer (the substituents CN and OR' are at same side in double bond B) and E isomer (the substituents CN and $OR_1$ are at different side in double bond B), can be present according to the different reaction condition or starting materials. A certain stereoisomer as the major product or a single configuration product can be obtained by selecting appropriate starting materials or by controlling reaction condition. Single configuration product also can be obtained by isolating the crude product through column chromatography, recrystallization or other isolating methods. The stereoisomers structures were characterized by X-ray diffraction analyses, NMR or other analysis methods.

Some compounds and its streroisomer in the invention were characterized by X-ray diffraction analyses. Testing compound was dissolved in a certain solvent, and the crystal was afforded with solvent evaporation slowly at room temperature. A appropriate size crystal was selected for the X-ray diffraction at BRUKER SMART 1000 CCD diffractometer. The diffraction data was collected at 293(2) K, and MoKα (λ0.71073 Å) as arrival of radiation within 2.01°≦θ≦25.03°, ω-2θ as the scan mode. The X-ray diffraction intensity data was corrected by Lp factor and experience absorb. The structure was solved by direct method and refined by block-diagonal least squares method. Non-hydrogen atoms were determined by Fourier synthesis. Hydrogen atoms were determined by theory method and participated the calculation of structure factor. All calculation was implemented by the procedure of SHELXL-97 and afforded the deviation factor R, wR and molecule structure at last.

Table 1 shows the structures and their physical properties of some representative compounds of general formula I:

TABLE 1

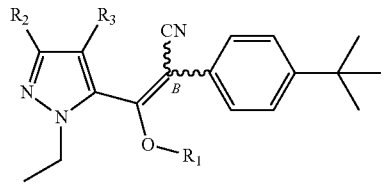

I

| Compd | R₁ | R₂ | R₃ | Configuration | Appearance (m.p.(° C.)) |
|---|---|---|---|---|---|
| 1 | H | CH₃ | H | | yellow solid (70-72° C.) |
| 2 | CH₂OCH₃ | CH₃ | H | | |
| 3 | CH₂OCH₂CH₃ | CH₃ | H | | |
| 4 | CH₂CH₂OCH₃ | CH₃ | H | | |
| 5.1 | COC(CH₃)₃ | CH₃ | H | Z | white solid (92-93° C.) |
| 5.2 | COC(CH₃)₃ | CH₃ | H | E | white solid (121-123° C.) |
| 6.1 | COC(CH₃)₂CH₂CH₃ | CH₃ | H | Z | yellow oil |
| 6.2 | COC(CH₃)₂CH₂CH₃ | CH₃ | H | E | yellow oil |
| 7.1 | [cyclopropyl ketone] | CH₃ | H | Z | yellow oil |
| 7.2 | [cyclopropyl ketone] | CH₃ | H | E | yellow oil |
| 8 | [methylcyclopropyl ketone] | CH₃ | H | | |
| 9 | [dimethylcyclopropyl ketone] | CH₃ | H | | |
| 10 | [dimethylcyclopropyl ketone] | CH₃ | H | | |
| 11 | [trimethylcyclopropyl ketone] | CH₃ | H | | |
| 12 | [tetramethylcyclopropyl ketone] | CH₃ | H | | |
| 13.1 | [cyclobutyl ketone] | CH₃ | H | Z | yellow oil |
| 13.2 | [cyclobutyl ketone] | CH₃ | H | E | yellow oil |
| 14 | [cyclopentyl ketone] | CH₃ | H | | |
| 15 | [cyclohexyl ketone] | CH₃ | H | | |
| 16 | COOCH₃ | CH₃ | H | | |
| 17.1 | COOCH₂CH₃ | CH₃ | H | Z | white solid (96-97° C.) |
| 17.2 | COOCH₂CH₃ | CH₃ | H | E | yellow oil |
| 18 | COOCH(CH₃)CH₃ | CH₃ | H | | |
| 19 | COOC(CH₃)₃ | CH₃ | H | | |
| 20 | H | Cl | H | | |
| 21 | CH₂OCH₃ | Cl | H | | |
| 22 | CH₂OCH₂CH₃ | Cl | H | | |
| 23 | CH₂CH₂OCH₃ | Cl | H | | |
| 24 | COC(CH₃)₃ | Cl | H | | |
| 25 | COC(CH₃)₂CH₂CH₃ | Cl | H | | |
| 26 | [cyclopropyl ketone] | Cl | H | | |
| 27 | [methylcyclopropyl ketone] | Cl | H | | |
| 28 | [dimethylcyclopropyl ketone] | Cl | H | | |
| 29 | [trimethylcyclopropyl ketone] | Cl | H | | |

TABLE 1-continued

I

| Compd | R₁ | R₂ | R₃ | Configuration | Appearance (m.p.(° C.)) |
|---|---|---|---|---|---|
| 30 | (2,2-dimethylcyclopropyl)carbonyl | Cl | H | | |
| 31 | (2,2,3,3-tetramethylcyclopropyl)carbonyl | Cl | H | | |
| 32 | cyclobutylcarbonyl | Cl | H | | |
| 33 | cyclopentylcarbonyl | Cl | H | | |
| 34 | cyclohexylcarbonyl | Cl | H | | |
| 35 | COOCH₃ | Cl | H | | |
| 36 | COOCH₂CH₃ | Cl | H | | |
| 37 | COOCH(CH₃)CH₃ | Cl | H | | |
| 38 | COOC(CH₃)₃ | Cl | H | | |
| 39 | H | CH₃ | CH₃ | | yellow solid (86-88° C.) |
| 40.1 | CH₂OCH₃ | CH₃ | CH₃ | Z | |
| 40.2 | CH₂OCH₃ | CH₃ | CH₃ | E | |
| 41 | CH₂OCH₂CH₃ | CH₃ | CH₃ | | |
| 42.1 | COC(CH₃)₃ | CH₃ | CH₃ | Z | yellow oil |
| 42.2 | COC(CH₃)₃ | CH₃ | CH₃ | E | yellow oil |
| 43.1 | COC(CH₃)₂CH₂CH₃ | CH₃ | CH₃ | Z | yellow oil |
| 43.2 | COC(CH₃)₂CH₂CH₃ | CH₃ | CH₃ | E | yellow oil |
| 44.1 | cyclopropylcarbonyl | CH₃ | CH₃ | Z | yellow oil |
| 44.2 | cyclopropylcarbonyl | CH₃ | CH₃ | E | yellow oil |
| 45 | (2-methylcyclopropyl)carbonyl | CH₃ | CH₃ | | |
| 46 | (2,2-dimethylcyclopropyl)carbonyl | CH₃ | CH₃ | | |
| 47 | (2,3-dimethylcyclopropyl)carbonyl | CH₃ | CH₃ | | |
| 48 | (2,2-dimethylcyclopropyl)carbonyl | CH₃ | CH₃ | | |
| 49 | (2,2,3,3-tetramethylcyclopropyl)carbonyl | CH₃ | CH₃ | | |
| 50.1 | cyclobutylcarbonyl | CH₃ | CH₃ | Z | yellow oil |
| 50.2 | cyclobutylcarbonyl | CH₃ | CH₃ | E | yellow oil |
| 51 | cyclopentylcarbonyl | CH₃ | CH₃ | | |
| 52 | cyclohexylcarbonyl | CH₃ | CH₃ | | |
| 53 | COOCH₃ | CH₃ | CH₃ | | |
| 54.1 | COOCH₂CH₃ | CH₃ | CH₃ | Z | yellow oil |
| 54.2 | COOCH₂CH₃ | CH₃ | CH₃ | E | yellow oil |
| 55 | COOCH(CH₃)CH₃ | CH₃ | CH₃ | | |
| 56 | COOC(CH₃)₃ | CH₃ | CH₃ | | |
| 57 | H | Cl | CH₃ | | |
| 58 | CH₂OCH₃ | Cl | CH₃ | | |
| 59 | CH₂OCH₂CH₃ | Cl | CH₃ | | |
| 60 | CH₂CH₂OCH₃ | Cl | CH₃ | | |
| 61 | COC(CH₃)₃ | Cl | CH₃ | | |
| 62 | COC(CH₃)₂CH₂CH₃ | Cl | CH₃ | | |
| 63 | cyclopropylcarbonyl | Cl | CH₃ | | |
| 64 | (2-methylcyclopropyl)carbonyl | Cl | CH₃ | | |

TABLE 1-continued

| Compd | R₁ | R₂ | R₃ | Configuration | Appearance (m.p.(° C.)) |
|---|---|---|---|---|---|
| 65 | cyclopropylcarbonyl | Cl | CH₃ | | |
| 66 | (methyl)cyclopropylcarbonyl | Cl | CH₃ | | |
| 67 | (dimethyl)cyclopropylcarbonyl | Cl | CH₃ | | |
| 68 | (trimethyl)cyclopropylcarbonyl | Cl | CH₃ | | |
| 69 | cyclobutylcarbonyl | Cl | CH₃ | | |
| 70 | cyclopentylcarbonyl | Cl | CH₃ | | |
| 71 | cyclohexylcarbonyl | Cl | CH₃ | | |
| 72 | COOCH₃ | Cl | CH₃ | | |
| 73 | COOCH₂CH₃ | Cl | CH₃ | | |
| 74 | COOCH(CH₃)₂ | Cl | CH₃ | | |
| 75 | COOC(CH₃)₃ | Cl | CH₃ | | |
| 76 | H | CH₃ | CN | | yellow oil |
| 77.1 | COC(CH₃)₃ | CH₃ | CN | Z | yellow oil |
| 77.2 | COC(CH₃)₃ | CH₃ | CN | E | yellow oil |
| 78.1 | COC(CH₃)₂CH₂CH₃ | CH₃ | CN | Z | yellow oil |
| 78.2 | COC(CH₃)₂CH₂CH₃ | CH₃ | CN | E | yellow oil |
| 79.1 | cyclopropylcarbonyl | CH₃ | CN | Z | yellow oil |
| 79.2 | cyclopropylcarbonyl | CH₃ | CN | E | yellow oil |
| 80.1 | cyclobutylcarbonyl | CH₃ | CN | Z | yellow oil |
| 80.2 | cyclobutylcarbonyl | CH₃ | CN | E | yellow oil |
| 81 | H | CH₃ | F | | yellow oil |
| 82.1 | COC(CH₃)₃ | CH₃ | F | Z | yellow oil |
| 82.2 | COC(CH₃)₃ | CH₃ | F | E | yellow oil |
| 83.1 | COC(CH₃)₂CH₂CH₃ | CH₃ | F | Z | yellow oil |
| 83.2 | COC(CH₃)₂CH₂CH₃ | CH₃ | F | E | yellow oil |
| 84.1 | cyclopropylcarbonyl | CH₃ | F | Z | yellow oil |
| 84.2 | cyclopropylcarbonyl | CH₃ | F | E | yellow oil |
| 85.1 | cyclobutylcarbonyl | CH₃ | F | Z | yellow oil |
| 85.2 | cyclobutylcarbonyl | CH₃ | F | E | yellow oil |
| 86 | H | CH₃ | Cl | | yellow oil |
| 87.1 | CH₂OCH₃ | CH₃ | Cl | Z | yellow oil |
| 87.2 | CH₂OCH₃ | CH₃ | Cl | E | yellow oil |
| 88 | CH₂OCH₂CH₃ | CH₃ | Cl | | |
| 89 | CH₂CH₂OCH₃ | CH₃ | Cl | | |
| 90.1 | COC(CH₃)₃ | CH₃ | Cl | Z | white solid (93-94° C.) |
| 90.2 | COC(CH₃)₃ | CH₃ | Cl | E | white solid (124-125° C.) |
| 91.1 | COC(CH₃)₂CH₂CH₃ | CH₃ | Cl | Z | yellow oil |
| 91.2 | COC(CH₃)₂CH₂CH₃ | CH₃ | Cl | E | yellow oil |
| 92.1 | cyclopropylcarbonyl | CH₃ | Cl | Z | yellow oil |
| 92.2 | cyclopropylcarbonyl | CH₃ | Cl | E | yellow oil |

TABLE 1-continued

Structure I: pyrazole with N-ethyl, R2 at 3-position, R3 at 4-position, connected at 5-position to C(OR1)=C(CN)(4-tert-butylphenyl), configuration at bond B.

| Compd | R1 | R2 | R3 | Configuration | Appearance (m.p.(° C.)) |
|---|---|---|---|---|---|
| 93 | C(=O)-(1-methylcyclopropyl) | CH3 | Cl | | |
| 94 | C(=O)-(2-methylcyclopropyl) | CH3 | Cl | | |
| 95 | C(=O)-(1,2-dimethylcyclopropyl) | CH3 | Cl | | |
| 96 | C(=O)-(2,2-dimethylcyclopropyl) | CH3 | Cl | | |
| 97.1 | C(=O)-cyclobutyl | CH3 | Cl | Z | yellow oil |
| 97.2 | C(=O)-cyclobutyl | CH3 | Cl | E | yellow oil |
| 98 | C(=O)-cyclopentyl | CH3 | Cl | | |
| 99 | C(=O)-cyclohexyl | CH3 | Cl | | |
| 100 | COOCH3 | CH3 | Cl | | |
| 101.1 | COOCH2CH3 | CH3 | Cl | Z | yellow oil |
| 101.2 | COOCH2CH3 | CH3 | Cl | E | yellow oil |
| 102 | COOCH(CH3)CH3 | CH3 | Cl | | |
| 103 | COOC(CH3)3 | CH3 | Cl | | |
| 104 | H | Cl | Cl | | |
| 105 | CH2OCH3 | Cl | Cl | | |
| 106 | CH2OCH2CH3 | Cl | Cl | | |
| 107 | CH2CH2OCH3 | Cl | Cl | | |
| 108 | COC(CH3)3 | Cl | Cl | | |
| 109 | COC(CH3)2CH2CH3 | Cl | Cl | | |
| 110 | C(=O)-cyclopropyl | Cl | Cl | | |
| 111 | C(=O)-(1-methylcyclopropyl) | Cl | Cl | | |
| 112 | C(=O)-(2-methylcyclopropyl) | Cl | Cl | | |
| 113 | C(=O)-(1,2-dimethylcyclopropyl) | Cl | Cl | | |
| 114 | C(=O)-(2,2-dimethylcyclopropyl) | Cl | Cl | | |
| 115 | C(=O)-(tetramethylcyclopropyl) | Cl | Cl | | |
| 116 | C(=O)-cyclobutyl | Cl | Cl | | |
| 117 | C(=O)-cyclopentyl | Cl | Cl | | |
| 118 | C(=O)-cyclohexyl | Cl | Cl | | |
| 119 | COOCH3 | Cl | Cl | | |
| 120 | COOCH2CH3 | Cl | Cl | | |
| 121 | COOCH(CH3)CH3 | Cl | Cl | | |
| 122 | COOC(CH3)3 | Cl | Cl | | |
| 123 | H | CH3 | Br | | yellow oil |
| 124.1 | COC(CH3)3 | CH3 | Br | Z | yellow oil |
| 124.2 | COC(CH3)3 | CH3 | Br | E | yellow oil |
| 125.1 | COC(CH3)2CH2CH3 | CH3 | Br | Z | yellow oil |
| 125.2 | COC(CH3)2CH2CH3 | CH3 | Br | E | yellow oil |
| 126.1 | C(=O)-cyclopropyl | CH3 | Br | Z | yellow oil |

TABLE 1-continued

| Compd | R₁ | R₂ | R₃ | Config-uration | Appearance (m.p.(° C.)) |
|---|---|---|---|---|---|
| 126.2 | —C(O)-cyclopropyl | CH₃ | Br | E | yellow oil |
| 127.1 | —C(O)-cyclobutyl | CH₃ | Br | Z | yellow oil |
| 127.2 | —C(O)-cyclobutyl | CH₃ | Br | E | yellow oil |
| 128 | COC(CH₃)₃ | CH₃ | I | | |
| 129 | H | CH₃ | NO₂ | | yellow oil |
| 130 | COC(CH₃)₃ | CH₃ | NO₂ | | |

$^1$H NMR (300 MHz, CDCl$_3$) data of some representative compounds are as follows:

Compound 1: 7.43 (d, 2H), 7.34 (d, 2H), 6.70 (s, 1H), 5.26 (s, 1H), 4.46 (q, 2H), 2.28 (s, 3H), 1.34 (t, 3H), 1.30 (s, 9H).

Compound 5.1: 7.32 (d, 2H), 7.07 (d, 2H), 6.18 (s, 1H), 3.57 (q, 2H), 2.28 (s, 3H), 1.36 (s, 9H), 1.27 (s, 9H), 1.01 (t, 3H).

Compound 5.2: 7.46 (d, 2H), 7.45 (d, 2H), 6.36 (s, 1H), 4.25 (q, 2H), 2.31 (s, 3H), 1.54 (t, 3H), 1.34 (s, 9H), 1.14 (s, 9H).

Compound 6.1: 7.31 (d, 2H), 7.07 (d, 2H), 6.19 (s, 1H), 3.57 (q, 2H), 2.29 (s, 3H), 1.72 (q, 2H), 1.29 (s, 6H), 1.27 (s, 9H), 0.89 (t, 3H), 1.00 (t, 3H).

Compound 6.2: 7.47 (d, 2H), 7.45 (d, 2H), 6.34 (s, 1H), 4.25 (q, 2H), 2.30 (s, 3H), 1.57-1.50 (m, 5H), 1.33 (s, 9H), 1.10 (s, 6H), 0.63 (t, 3H).

Compound 7.1: 7.31 (d, 2H), 7.08 (d, 2H), 6.18 (s, 1H), 3.60 (q, 2H), 1.84-1.80 (m, 1H), 1.25 (s, 9H), 1.20-1.08 (m, 5H), 1.04 (t, 3H).

Compound 7.2: 7.50 (d, 2H), 7.45 (d, 2H), 6.48 (s, 1H), 4.20 (q, 2H), 2.30 (s, 3H), 1.76-1.66 (m, 1H), 1.51 (t, 3H), 1.35 (s, 9H), 1.13-0.98 (m, 4H).

Compound 13.1: 7.32 (d, 2H), 7.09 (d, 2H), 6.18 (s, 1H), 3.61 (q, 2H), 2.50-2.30 (m, 4H), 2.34 (s, 3H), 2.10-1.94 (m, 2H), 1.27 (s, 9H), 1.04 (t, 3H).

Compound 13.2: 7.50 (d, 2H), 7.45 (d, 2H), 6.45 (s, 1H), 4.22 (q, 2H), 3.26-3.18 (m, 1H), 2.31 (s, 3H), 2.21-2.13 (m, 4H), 2.00-1.80 (m, 2H), 1.49 (t, 3H), 1.28 (s, 9H).

Compound 17.1: 7.33 (d, 2H), 7.10 (d, 2H), 6.25 (s, 1H), 4.28 (q, 2H), 3.63 (q, 2H), 2.29 (s, 3H), 1.36 (t, 3H), 1.28 (s, 9H), 1.06 (t, 3H).

Compound 17.2: 7.56 (d, 2H), 7.48 (d, 2H), 6.54 (s, 1H), 4.30-4.10 (m, 4H), 2.31 (s, 3H), 1.49 (t, 3H), 1.34 (s, 9H), 1.23 (t, 3H).

Compound 39: 7.93 (d, 2H), 7.48 (d, 2H), 4.20-4.00 (m, 2H), 2.10 (s, 3H), 2.09 (s, 3H), 1.36 (s, 9H), 1.24 (t, 3H).

Compound 42.1: 7.30 (d, 2H), 7.04 (d, 2H), 3.90-3.60 (m, 2H), 2.18 (s, 3H), 1.84 (s, 3H), 1.35 (s, 9H), 1.27 (s, 9H), 1.13 (t, 3H).

Compound 42.2: 7.48 (d, 2H), 7.46 (d, 2H), 4.20-4.10 (m, 2H), 2.23 (s, 3H), 2.12 (s, 3H), 1.48 (t, 3H), 1.34 (s, 9H), 1.15 (s, 9H).

Compound 43.1: 7.30 (d, 2H), 7.04 (d, 2H), 4.00-3.60 (m, 2H), 2.18 (s, 3H), 1.85 (s, 3H), 1.75 (q, 2H), 1.29 (s, 6H), 1.27 (s, 9H), 1.12 (t, 3H), 0.89 (t, 3H).

Compound 43.2: 7.50 (d, 2H), 7.44 (d, 2H), 4.17 (q, 2H), 2.22 (s, 3H), 2.13 (s, 3H), 1.49 (q, 5H), 1.33 (s, 9H), 1.11 (s, 6H), 0.61 (t, 3H).

Compound 44.1: 7.29 (d, 2H), 7.06 (d, 2H), 3.90-3.60 (br, 2H), 2.16 (s, 3H), 1.90-1.80 (m, 1H), 1.79 (s, 3H), 1.27 (s, 9H), 1.18 (d, 4H), 1.07 (m, 3H).

Compound 44.2: 7.55 (dd, 2H,), 7.47 (dd, 2H), 4.14 (q, 2H), 2.22 (s, 3H), 2.11 (s, 3H), 1.80-1.60 (m, 1H), 1.48 (t, 3H), 1.35 (s, 9H), 1.27 (d, 2H), 0.95 (d, 2H).

Compound 50.1: 7.30 (d, 2H), 7.06 (d, 2H), 4.00-3.60 (br, 2H), 3.40-3.10 (m, 1H), 2.50-2.00 (m, 6H), 2.17 (s, 3H), 1.79 (s, 3H), 1.27 (s, 9H), 1.16 (t, 3H).

Compound 50.2: 7.52 (d, 2H), 7.45 (d, 2H), 4.13 (q, 2H), 3.22 (m, 1H), 2.23 (s, 3H), 2.12 (s, 3H), 2.00-1.60 (m, 6H), 1.34 (s, 9H), 0.96 (t, 3H).

Compound 54.1: 7.30 (d, 2H), 7.08 (d, 2H), 4.27 (q, 2H), 3.90-3.70 (br s, 2H), 2.17 (s, 3H), 1.77 (s, 3H), 1.35 (t, 3H), 1.27 (s, 9H), 1.19 (t, 3H).

Compound 54.2: 7.61 (d, 2H), 7.48 (d, 2H), 4.22-4.14 (m, 4H), 2.24 (s, 3H), 2.13 (s, 3H), 1.45 (t, 3H), 1.35 (s, 9H), 1.24 (t, 3H).

Compound 77.1: 7.36 (d, 2H), 7.05 (d, 2H), 3.76-3.64 (m, 1H), 3.52-3.42 (m, 1H), 2.41 (s, 3H), 1.38 (s, 9H), 1.27 (s, 9H), 0.97 (t, 3H).

Compound 77.2: 7.56 (d, 2H), 7.50 (d, 2H), 4.30 (q, 2H), 2.43 (s, 3H), 1.61 (t, 3H), 1.35 (s, 9H), 1.25 (s, 9H).

Compound 78.1: 7.36 (d, 2H), 7.05 (d, 2H), 3.76-3.64 (m, 1H), 3.52-3.42 (m, 1H), 2.41 (s, 3H), 1.78 (q, 2H), 1.35 (s, 6H), 1.30 (s, 9H), 0.96 (t, 3H), 0.93 (t, 3H).

Compound 78.2: 7.55 (d, 2H), 7.49 (d, 2H), 4.30 (q, 2H), 2.43 (s, 3H), 1.64-1.58 (m, 5H), 1.28 (s, 9H), 1.19 (s, 6H), 0.70 (t, 3H).

Compound 79.1: 7.33 (d, 2H), 7.07 (d, 2H), 3.58 (q, 2H), 2.40 (s, 3H), 1.88-1.80 (m, 1H), 1.26 (s, 9H), 1.24-1.10 (m, 4H), 0.98 (t, 3H).

Compound 79.2: 7.51 (d, 2H), 7.45 (d, 2H), 4.12 (q, 2H), 2.27 (s, 3H), 1.80-1.66 (m, 1H), 1.47 (t, 3H), 1.33 (s, 9H), 1.08-1.02 (m, 4H).

Compound 80.1: 7.18 (d, 2H), 7.26 (d, 2H), 4.20 (q, 2H), 3.42 (q, 1H), 2.42 (s, 3H), 2.38-2.22 (m, 4H), 2.06-1.80 (m, 2H), 1.62 (t, 3H), 1.34 (s, 9H).

Compound 80.2: 7.58 (d, 2H), 7.48 (d, 2H), 4.28 (q, 2H), 3.40-3.30 (m, 1H), 2.42 (s, 3H), 2.36-2.22 (m, 4H), 2.06-1.84 (m, 2H), 1.59 (t, 3H), 1.33 (s, 9H).

Compound 82.1: 7.34 (d, 2H), 7.14 (d, 2H), 3.52 (q, 2H), 2.22 (s, 3H), 1.36 (s, 9H), 1.28 (s, 9H), 1.02 (t, 3H).

Compound 82.2: 7.50 (d, 2H), 7.46 (d, 2H), 4.16 (q, 2H), 2.23 (s, 3H), 1.51 (t, 3H), 1.34 (s, 9H), 1.23 (s, 9H).

Compound 83.1: 7.32 (d, 2H), 7.15 (d, 2H), 4.16 (q, 2H), 2.26 (s, 3H), 1.72 (q, 2H), 1.33 (s, 6H), 1.30 (s, 9H), 1.00 (t, 3H), 0.92 (t, 3H).

Compound 83.2: 7.50 (d, 2H), 7.46 (d, 2H), 4.25 (q, 2H), 2.28 (s, 3H), 1.58-1.53 (m, 5H), 1.34 (s, 9H), 1.15 (s, 6H), 0.66 (t, 3H).

Compound 84.1: 7.33 (d, 2H), 7.14 (d, 2H), 3.58 (q, 2H), 2.21 (s, 3H), 1.88-1.80 (m, 1H), 1.25 (s, 9H), 1.30-1.10 (m, 4H), 1.06 (t, 3H).

Compound 84.2: 7.51 (d, 2H), 7.45 (d, 2H), 4.12 (q, 2H), 2.27 (s, 3H), 1.80-1.66 (m, 1H), 1.47 (t, 3H), 1.33 (s, 9H), 1.03-1.01 (m, 4H).

Compound 85.1: 7.34 (d, 2H), 7.15 (d, 2H), 3.57 (q, 2H), 3.42-3.36 (m, 1H), 2.50-2.30 (m, 4H), 2.22 (s, 3H), 2.10-1.95 (m, 2H), 1.28 (s, 9H), 1.06 (t, 3H).

Compound 85.2: 7.49 (d, 2H), 7.43 (d, 2H), 4.12 (q, 2H), 3.30-3.28 (m, 1H), 2.26 (s, 3H), 2.25-2.18 (m, 4H), 2.06-1.80 (m, 2H), 1.47 (t, 3H), 1.33 (s, 9H).

Compound 87.1.1: 7.26 (d, 2H), 7.00 (d, 2H), 4.90 (q, 2H), 3.62 (s, 3H), 3.80-3.40 (m, 2H), 2.26 (s, 3H), 1.26 (s, 9H), 1.04 (t, 3H).

Compound 87.2: 7.87 (d, 2H), 7.48 (d, 2H), 5.00-4.80 (q, 2H), 4.10 (q, 2H), 3.42 (s, 3H), 2.30 (s, 3H), 1.49 (t, 3H), 1.35 (s, 9H).

Compound 90.1: 7.29 (d, 2H), 7.06 (d, 2H), 3.80-3.40 (m, 2H), 2.25 (s, 3H), 1.36 (s, 9H), 1.27 (s, 9H), 0.98 (t, 3H).

Compound 90.2: 7.53 (d, 2H), 7.47 (d, 2H), 4.21 (q, 2H), 2.27 (s, 3H), 1.55 (t, 3H), 1.34 (s, 9H), 1.20 (s, 9H).

Compound 91.1: 7.32 (d, 2H), 7.06 (d, 2H), 3.80-3.40 (m, 2H), 2.25 (s, 3H), 1.74 (q, 2H), 1.27 (s, 6H), 1.22 (s, 9H), 1.15-0.87 (m, 6H).

Compound 91.2: 7.53 (d, 2H), 7.47 (d, 2H), 4.23 (q, 2H), 2.27 (s, 3H), 1.61-1.53 (m, 5H), 1.34 (s, 9H), 1.15 (s, 6H), 0.66 (t, 3H).

Compound 92.1: 7.32 (d, 2H), 7.07 (d, 2H), 3.82-3.76 (m, 1H), 3.58-3.42 (m, 1H), 2.24 (s, 3H), 1.88-1.78 (m, 1H), 1.35 (s, 9H), 1.25-1.03 (m, 4H), 1.04 (t, 3H).

Compound 92.2: 7.59 (d, 2H), 7.49 (d, 2H), 4.19 (q, 2H), 2.28 (s, 3H), 1.80-1.70 (m, 1H), 1.50 (t, 3H), 1.35 (s, 9H), 1.07-1.01 (m, 4H).

Compound 97.1: 7.32 (d, 2H), 7.07 (d, 2H), 3.80-3.70 (m, 1H), 3.50-3.40 (m, 1H), 3.42-3.34 (m, 1H), 2.45-2.33 (m, 4H), 2.32 (s, 3H), 2.03-2.00 (m, 2H), 1.27 (s, 9H), 1.01 (t, 3H).

Compound 97.2: 7.55 (d, 2H), 7.48 (d, 2H), 4.23 (t, 2H), 3.30-3.20 (m, 1H), 2.27 (s, 3H), 2.27-2.20 (m, 4H), 2.04-1.80 (m, 2H), 1.52 (t, 3H), 1.34 (s, 9H).

Compound 101.1: 7.33 (d, 2H), 7.10 (d, 2H), 4.30 (q, 2H), 3.50-4.00 (br, 2H), 2.25 (s, 3H), 1.36 (t, 3H), 1.28 (s, 9H), 1.08 (t, 3H).

Compound 101.2: 7.64 (d, 2H), 7.49 (d, 2H), 4.25-4.15 (m, 4H), 2.29 (s, 3H), 1.49 (t, 3H), 1.35 (s, 9H), 1.26 (t, 3H).

Compound 124.1: 7.32 (d, 2H), 7.04 (d, 2H), 3.80 (q, 1H), 3.48 (q, 1H), 2.26 (s, 3H), 1.36 (s, 9H), 1.27 (s, 9H), 0.96 (t, 3H).

Compound 124.2: 7.54 (d, 2H), 7.46 (d, 2H), 4.24 (q, 2H), 2.28 (s, 3H), 1.56 (t, 3H), 1.34 (s, 9H), 1.20 (s, 9H).

Compound 125.1: 7.32 (d, 2H), 7.04 (d, 2H), 3.48 (q, 1H), 3.80 (q, 1H), 2.26 (s, 3H), 1.73 (q, 2H), 1.30 (s, 6H), 1.27 (s, 9H), 0.94 (t, 3H), 0.90 (t, 3H).

Compound 125.2: 7.51 (d, 2H), 7.44 (d, 2H), 4.25 (q, 2H), 2.28 (s, 3H), 1.58-1.53 (m, 5H), 1.34 (s, 9H), 1.15 (s, 6H), 0.66 (t, 3H).

Compound 126.1: 7.32 (d, 2H), 7.05 (d, 2H), 3.82-3.76 (m, 1H), 3.58-3.42 (m, 1H), 2.25 (s, 3H), 1.88-1.78 (m, 1H), 1.27 (s, 9H), 1.27-1.08 (m, 4H), 0.99 (t, 3H).

Compound 126.2: 7.59 (d, 2H), 7.50 (d, 2H), 4.21 (q, 2H), 2.28 (s, 3H), 1.80-1.70 (m, 1H), 1.51 (t, 3H), 1.34 (s, 9H), 1.09-1.00 (m, 4H).

Compound 127.1: 7.32 (d, 2H), 7.06 (d, 2H), 3.80-3.70 (m, 1H), 3.50-3.40 (m, 1H), 3.42-3.34 (m, 1H), 2.50-2.30 (m, 4H), 2.25 (s, 3H), 2.10-1.90 (m, 2H), 1.25 (s, 9H), 0.99 (t, 3H).

Compound 127.2: 7.57 (d, 2H), 7.47 (d, 2H), 4.23 (t, 2H), 3.35-3.20 (m, 1H), 2.28 (s, 3H), 2.30-2.18 (m, 4H), 2.04-1.80 (m, 2H), 1.53 (t, 3H), 1.34 (s, 9H).

Although the methyl and ethyl in organic molecule possess the similar chemical properties, there are significant differences in their electronegativity, volume and space conformation because of the diffenence of the number of carbon atoms, which makes the whole molecule show remarkably different transportation or docking properties in the biological organisms such as insects, or plants. The suitable transportation and space conformation of bioactive molecules play an important role in the biological efficacy. The suitable transportation or space conformation of molecules is unpredictable, so it only can be discovered through extensively creative investigation.

The 1-ethyl pyrazolyl acrylonitrile compounds in the present invention possess surprisingly high insecticidal or acarididal activity against the following insect: diamondback moth (*Plutella xylostella* Linnaeus), beet armyworm (*Spodoptera exigua* Huibner), prodenia litura (*Fabricius*), corn earworm (*Helicoverpa zea* Boddie), mythimna separata (Walker), cabbage looper (*Trichoplusiani*, Tn), acyrthosiphonpisum, ahis glyeines (*Aphis craccivora* Koch), beet aphid (Pemphigus beatae), cotton aphid (*Aphis gossypii* Glover), apple aphid (*Aphis pomi* De Geer), peach aphid (*Myzus peisicae* Sulzer), rhopalosiphummaidis, whitefly, leafhopper, delphacidae, planthopper (*Nilaparvatalugens Stal*), pseudococcidae, stinkbug, rigonotylus, nezaraviridula (Linnaeus), cimicidae, thrips tabaci (Lindemen), potato beetle (*Leptinotarsa decemlineata*, Say), click beetle, fly, mosquito, mite, and other pests. Compared with the known compound such as 1-methylpyrazolyl acrylonitrile compound, the 1-ethyl pyrazolyl acrylonitrile compounds in the present invention possess surprisingly high acarididal activity against adult mite, deutonymph and egg of mite. Meanwhile, 1-ethyl pyrazolyl acrylonitrile compounds possess surprisingly transportation properties. Therefore, the present invention also provides the application of the general formula I compounds for controlling mites or insects.

Another embodiment of the present invention includes the insecticidal or acaricidal compositions, in which the compounds of general formula I are active ingredients. The weight percentage of active ingredient(s) in the compositions is from 1% to 99%. There are also acceptable carriers in agriculture, forestry or public health in these compositions.

The compositions of the present invention can be used in the form of various formulations. Usually, the compounds of general formula I as the active ingredient can be dissolved in or dispersed in carriers or made to a formulation, so that they can be easily dispersed as an insecticide, or a acaricide such as a wettable powder or an emulsifiable concentrate. Therefore, in these compositions, at least a liquid or solid carrier is added, and usually suitable surfactant(s) can be added when needed.

Still also provided by the present invention are the application methods for controlling insects or mites, which is to apply the compositions of the present invention to the growing loci of the insects or mites as mentioned above. The suitably effective dosage of the compounds of the present invention is usually within a range of 10 g/ha to 1000 g/ha, preferably from 50 g/ha to 500 g/ha.

For some applications, one or more other fungicides, insecticides, herbicides, plant growth regulators or fertilizer can be added into the insecticidal or acaricidal compositions of the present invention to make additional merits and effects.

It shall be noted that variations and changes are permitted within the claimed scopes in the present invention.

ATTACHED FIGURE

Figure 2:
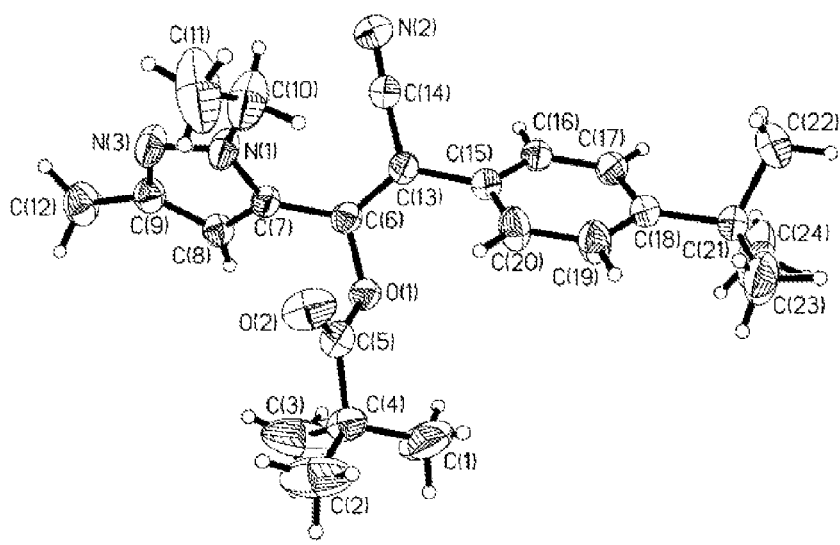

FIG. 1 the molecule structure of compound 5.1.
FIG. 2 the molecule structure of compound 5.2.

Figure 3:
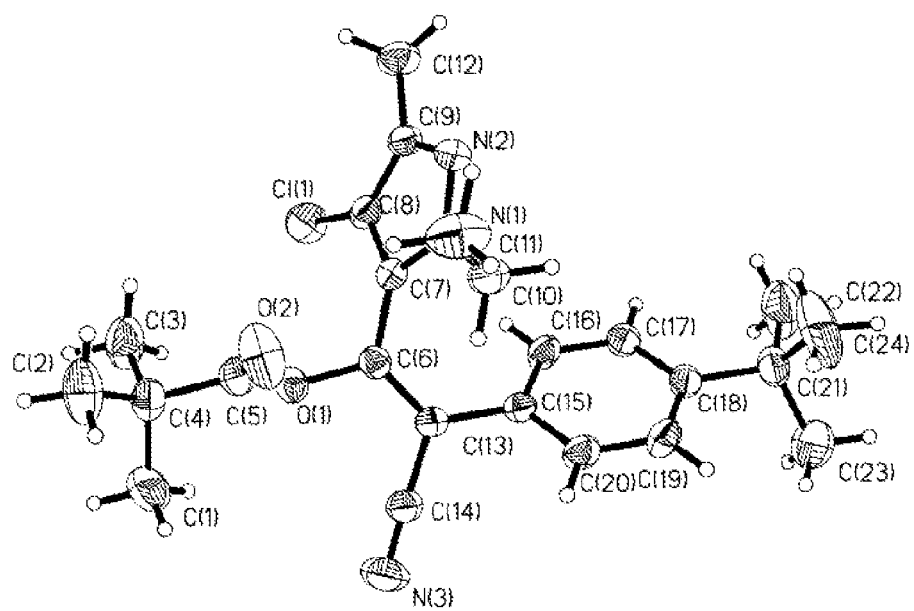

FIG. 3 the molecule structure of compound 90.1.

Figure 4:
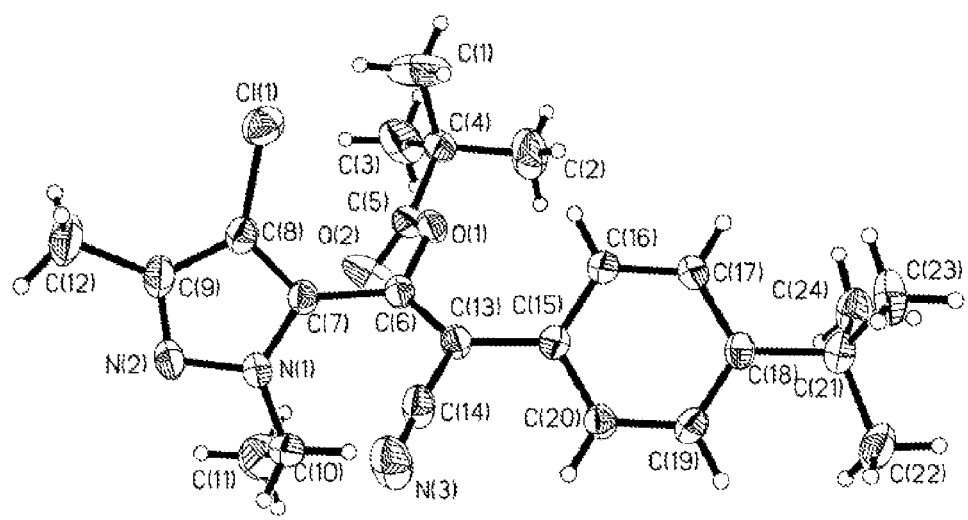

FIG. 4 the molecule structure of compound 90.2.

Figure 5:
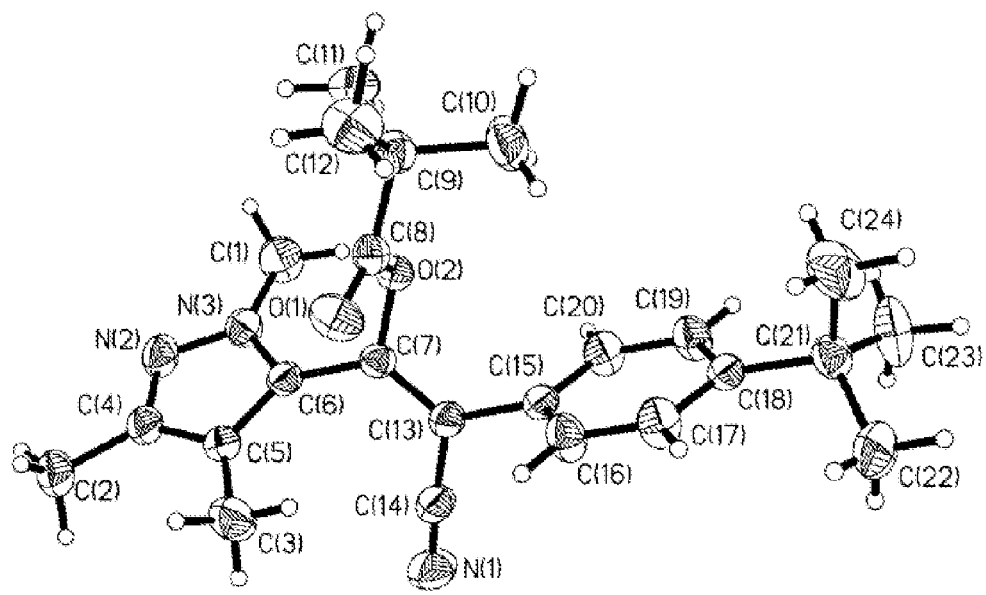

FIG. 5 the molecule structure of compound $KC_1$ (cyenopyrafen).

Figure 6:
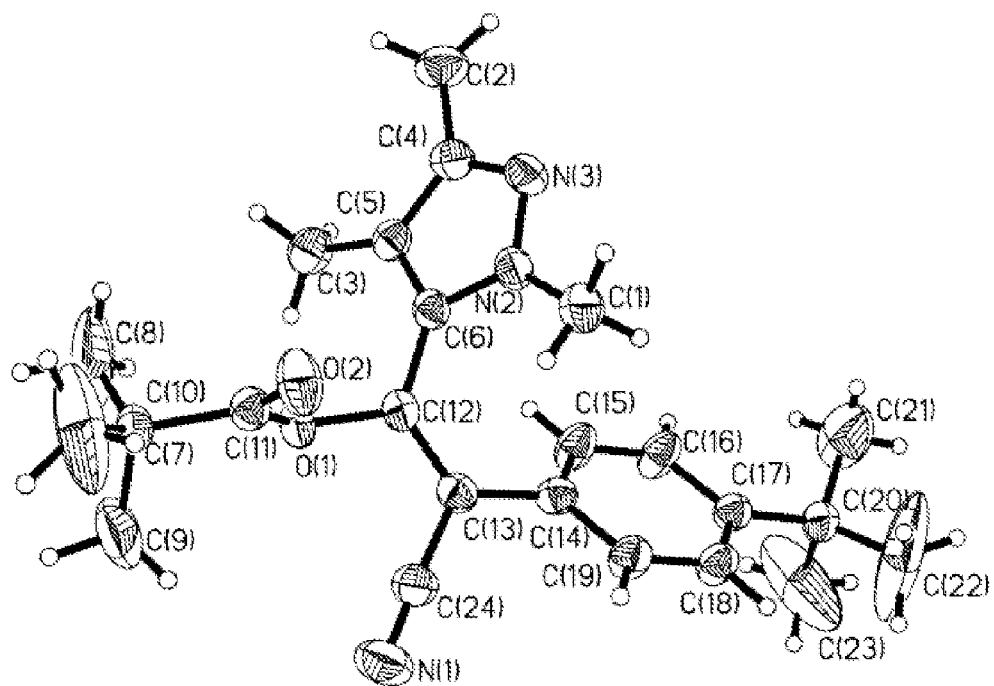

FIG. 6 the molecule structure of compound $KC_2$ (cyenopyrafen's isomer).

DESCRIPTION OF THE INVENTION IN DETAIL

The following synthesis examples and results of biological tests are used to further illustrate the present invention, but not to limit it.

SYNTHESIS EXAMPLES

Example 1

Synthesis of Compound 1, 5.1, 5.2

(1) Synthesis of Compound 1

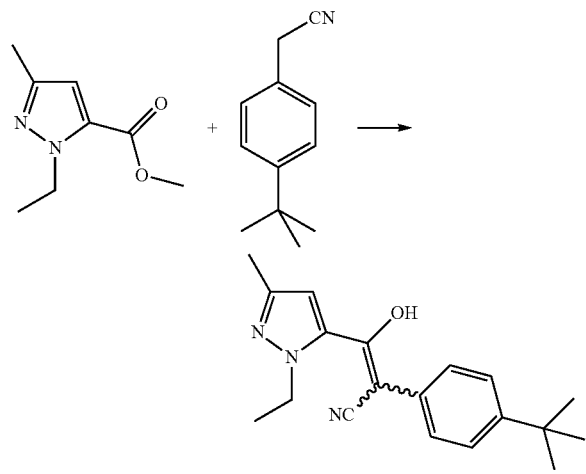

A mixture of methyl 1-ethyl-3-methylpyrazol-5-ylcarboxylate (3.63 g, 0.021 mol, Ref. CN1626520A), p-tertbutylphenylacetonitrile (3.29 g, 0.019 mol, Ref. Org. Syn., Coll. 1941, 1, 107; Org. Syn., Coll. 1922, 2, 9), ethylene glycol ethyl ether (4 mL) in heptane (40 mL) was stirred at room temperature under the atmosphere of nitrogen in the flask with Dean-Srark trap, then azeotropic dehydration was carried out under heating to reflux for 1 h. To the reaction mixture, 20% sodium methoxide methanol solution (5.71 g, 0.028 mol) was dropwised, and the resulting mixture was further reacted for 6 h under refluxing. After cooling to 30° C., the resulting mixture was extracted with 150 mL of water and 100 mL of ethyl acetate. The aqueous layer was acidified to pH 2~3 by concentrated hydrochloric acid and extracted with ethyl acetate (3×150 mL). The organic layer was washed with 150 mL of saturated aqueous sodium bicarbonate solution and 150 mL of saturated brine, dried over anhydrous $MgSO_4$, and concentrated under reduced pressure to obtain 2.50 g (yield 37%) of compound I as a yellow solid, m.p. 70~72° C.

(2) Synthesis of Compound 5.1 and 5.2

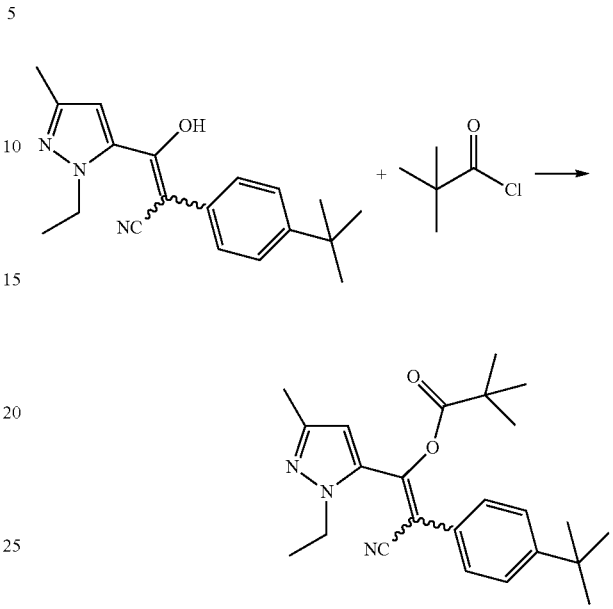

To the mixture of 3-(1-ethyl-3-methylpyrazol-5-yl)-2-(4-tertbutylphenyl)-3-hydroxy-acrylonitrile (1) (0.59 g, 0.002 mol), triethylamine (0.36 g, 0.003 mol) in 10 mL of $CH_2Cl_2$ in the flask, pivaloyl chloride (0.46 g, 0.003 mol) was added dropwise in ice-water bath, then stirred at r.t. for 2 h. After removal of the solvent under reduced pressure, the residue was partitioned between 100 mL of ethyl acetate and 50 mL of water, the organic layer was washed with 100 mL of saturated aqueous sodium bicarbonate solution and 100 mL of saturated brine, dried over anhydrous $MgSO_4$ and concentrated. Column chromatography (EtOAc:P.E.=1:10 as eluent) gave the compound 5.1 (white solid, 0.15 g, yield 20%, m.p. 92-93° C.) and 5.2 (white solid, 0.27 g, yield 36%, m.p. 121-123° C.), respectively.

The solution of compound 5.1 (0.1 g) dissolved in 5 mL of acetone, was slightly evaporated to obtain colourless crystal at r.t. The crystal was selected for the X-ray diffraction, which size was about 0.38 mm×0.32 mm×0.30 mm. The number of diffraction data amounts to 11999, and 4207 ($R_{int}$ 0.0175) are independent diffraction data. 4207 observable reflections (I>2σ(I)) were used to determine and refine structure. All calculation was implemented by the procedure of SHELXL-97 and afforded the deviation factor R 0.0459, wR 0.1212 and molecule structure of compound 5.1 at last.

The solution of compound 5.2 (0.1 g) dissolved in 5 mL of acetone, was slightly evaporated to obtain colourless crystal at r.t. The crystal was selected for the X-ray diffraction, which size was about 0.28 mm×0.22 mm×0.20 mm. The number of diffraction data amounts to 5980, and 4108 ($R_{int}$ 0.0124) are independent diffraction data. 4108 observable reflections (I>2σ(I)) were used to determine and refine structure. All calculation was implemented by the procedure of SHELXL-97 and afforded the deviation factor R 0.0761, wR 0.2175 and molecule structure of compound 5.2 at last.

Example 2

Synthesis of Compound 39, 42.1, 42.2

(1) Synthesis of Compound 39

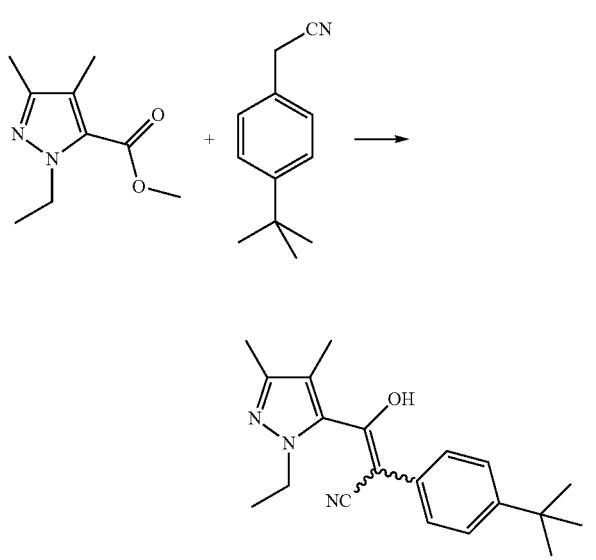

A mixture of methyl 1-ethyl-3,4-dimethylpyrazol-5-ylcarboxylate (6.00 g, 0.033 mol, Ref. JP2001342178A), p-tert-butylphenylacetonitrile (5.20 g, 0.030 mol), ethylene glycol ethyl ether (2.5 mL) in heptane (60 mL) was stirred at r.t. under the atmosphere of nitrogen in the flask with Dean-Stark trap, then azeotropic dehydration was carried out under heating to reflux for 1 h. To the reaction mixture, 20% sodium methoxide methanol solution (12.15 g, 0.045 mol) was dropwised, and the resulting mixture was further reacted for 5 h under reflux. After cooling to 30° C., the resulting mixture was extracted with 200 mL of water and 100 mL of ethyl acetate. The aqueous layer was acidified to pH 2~3 by concentrated hydrochloric acid and extracted with ethyl acetate (3×200 mL). The organic layer was washed with 200 mL of saturated aqueous sodium bicarbonate solution and 200 mL of saturated brine, dried over anhydrous $MgSO_4$, and concentrated under reduced pressure to obtain 7.37 g (yield 79%) compound 39 as a yellow solid, m.p. 86~88° C.

(2) Synthesis of Compound 42.1 and 42.2

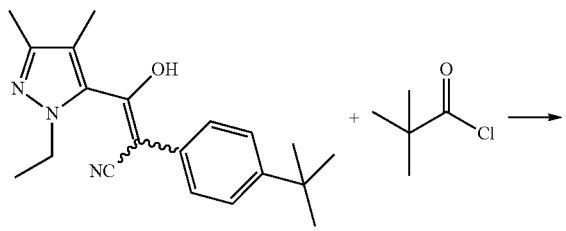

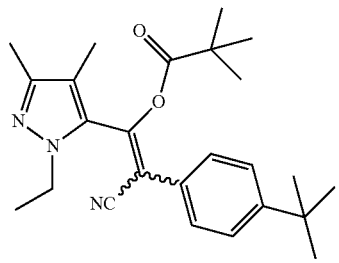

To the mixture of 3-(1-ethyl-3,4-dimethylpyrazol-5-yl)-2-(4-tertbutylphenyl)-3-hydroxyl-acrylonitrile (39) (0.60 g, 0.002 mol), triethylamine (0.30 g, 0.003 mol) in 10 mL of $CH_2Cl_2$ in the flask, pivaloyl chloride (0.36 g, 0.003 mol) was added dropwise in ice-water bath, then stirred at r.t. for 2 h. After removal of the solvent under reduced pressure, the residue was partitioned between 100 mL of ethyl acetate and 50 mL of water, the organic layer was washed with 100 mL of saturated aqueous sodium bicarbonate solution and 100 mL of saturated brine, dried over anhydrous $MgSO_4$ and concentrated. Column chromatography (EtOAc:P.E.=1:10 as eluent) gave the compound 42.1 (yellow oil, 0.10 g, yield 14%) and 42.2 (yellow oil, 0.20 g, yield 27%), respectively.

Example 3

Synthesis of Compound 76, 77.1, 77.2

(1) Synthesis of methyl 1-ethyl-4-iodo-3-methylpyrazol-5-ylcarboxylate

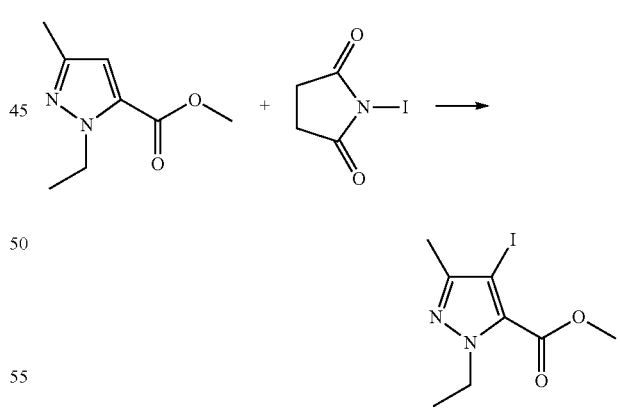

To a flask, methyl 1-ethyl-3-methylpyrazol-5-ylcarboxylate (1.00 g, 0.006 mol, Ref. CN1626520A) was dissolved in 10 mL of DMF and N-iodosuccinimide (1.47 g, 0.007 mol) was added in batches. After reacting for 8 h at r.t., the mixture was diluted with 50 mL of water, and then extracted with 50 mL of ethyl acetate. The organic layer was washed with 50 mL of saturated aqueous sodium bicarbonate solution and 50 mL of saturated brine, dried over anhydrous $MgSO_4$ and concentrated under reduced pressure. Column chromatography (EtOAc:P.E.=1:10 as eluent) gave 0.82 g of the title compound as a yellow oil (yield 47%).

(2) Synthesis of methyl 4-cyano-1-ethyl-3-methylpyrazol-5-ylcarboxylate

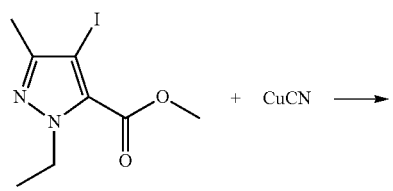

To a flask, methyl 1-ethyl-4-iodo-3-methylpyrazol-5-ylcarboxylate (1.00 g, 0.003 mol) was dissolved in 10 mL of DMF and copper (I) cyanide (0.46 g, 0.005 mol) was added in batches. After heating to reflux for 1 h, the mixture was separated by filtration. The filtrate was diluted with 50 mL of water, and then extracted with 50 mL of ethyl acetate. The organic layer was washed with 50 mL of saturated aqueous sodium bicarbonate solution and 50 mL of saturated brine, dried over anhydrous MgSO₄ and concentrated under reduced pressure. Column chromatography (EtOAc:P.E.=1:10 as eluent) gave 0.53 g of the title compound as a yellow oil (yield 80%).

(3) Synthesis of Compound 76

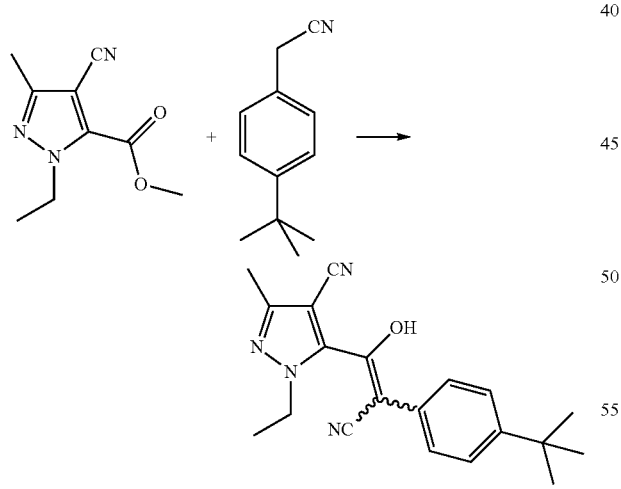

A mixture of methyl 4-cyano-1-ethyl-3-methylpyrazol-5-ylcarboxylate (1.42 g, 0.007 mol), p-tertbutylphenylacetonitrile (0.93 g, 0.005 mol), ethylene glycol ethyl ether (3 mL) in heptane (30 mL) was stirred at room temperature under the atmosphere of nitrogen in the flask with Dean-Stark trap, then azeotropic dehydration was carried out under heating to reflux for 1 h. To the reaction mixture, 20% sodium methoxide methanol solution (2.95 g, 0.011 mol) was dropwised, and the resulting mixture was further reacted for 4 h under reflux. After cooling to 30° C., the resulting mixture was extracted with 100 mL of water and 100 mL of ethyl acetate. The aqueous layer was acidified to pH 2-3 by concentrated hydrochloric acid and extracted with ethyl acetate (3×100 mL). The organic layer was washed with 200 mL of saturated aqueous sodium bicarbonate solution and 200 mL of saturated brine, dried over anhydrous MgSO₄, and concentrated under reduced pressure to obtain 1.60 g (yield 65%) compound 76 as a yellow oil.

(4) Synthesis of Compound 77.1 and 77.2

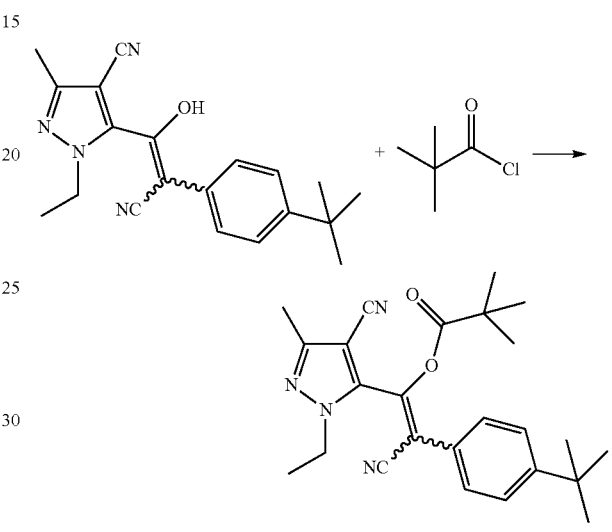

To the mixture of 3-(4-cyano-1-ethyl-3-methylpyrazol-5-yl)-2-(4-tertbutylphenyl)-3-hydroxy-acrylonitrile (76) (0.85 g, 0.002 mol), triethylamine (0.30 g, 0.002 mol) in 10 mL of THF in the flask, pivaloyl chloride (0.35 g, 0.003 mol) was added dropwise in ice-water bath, then stirred at r.t. for 2 h. After removal of the solvent under reduced pressure, the residue was partitioned between 100 mL of ethyl acetate and 50 mL of water, the organic layer was washed with 100 mL of saturated aqueous sodium bicarbonate solution and 100 mL of saturated brine, dried over anhydrous MgSO₄ and concentrated. Column chromatography (EtOAc:P.E.=1:20 as eluent) gave the compound 77.1 (yellow oil, 0.07 g, yield 7%) and 77.2 (yellow oil, 0.13 g, yield 12%), respectively.

Example 4

Synthesis of Compound 81, 82.1, 82.2

(1) Synthesis of methyl 1-ethyl-4-fluoro-3-methylpyrazol-5-ylcarboxylate

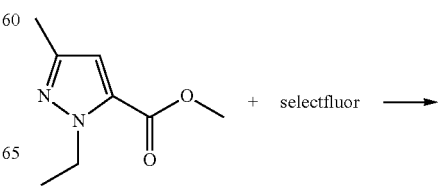

-continued

To a flask, methyl 1-ethyl-3-methylpyrazol-5-ylcarboxylate (1.70 g, 0.010 mol, Ref. CN1626520A) was dissolved in 30 mL of acetonitrile and the selectfluor (1-chloromethyl-4-fluoro-1,4-diazabicyclo[2.2.2]octanium bis(tetrafluoroborate)) (5.30 g, 0.015 mol) was added in batches. After heating to reflux for 1.5 h, the mixture was diluted with 50 mL of water, and then extracted with ethyl acetate (3×50 mL). The combined organic layer was washed with 150 mL of saturated aqueous sodium bicarbonate solution and 150 mL of saturated brine, dried over anhydrous MgSO$_4$ and concentrated under reduced pressure. Column chromatography (EtOAc:P.E.=1:20 as eluent) gave 0.50 g of the title compound as a yellow oil (yield 26%).

(2) Synthesis of Compound 81

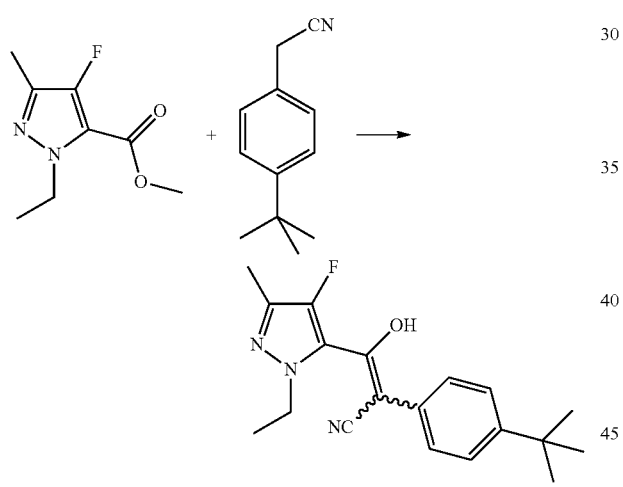

A mixture of methyl 1-ethyl-4-fluoro-3-methylpyrazol-5-ylcarboxylate (1.00 g, 0.005 mol), p-tertbutylphenylacetonitrile (0.67 g, 0.003 mol), ethylene glycol monoethyl ether (3 mL) in 30 mL of heptane was stirred at room temperature under the atmosphere of nitrogen in the flask with Dean-Stark trap, then azeotropic dehydration was carried out under heating to reflux for 1 h. To the reaction mixture, 20% sodium methoxide methanol solution (2.20 g, 0.008 mol) was dropwised, and the resulting mixture was further reacted for 4 h under reflux. After cooling to 30° C., the resulting mixture was extracted with 100 mL of water and 100 mL of ethyl acetate. The aqueous layer was acidified to pH 2~3 by concentrated hydrochloric acid and extracted with ethyl acetate (3×100 mL). The organic layer was washed with 200 mL of saturated aqueous sodium bicarbonate solution and 200 mL of saturated brine, dried over anhydrous MgSO$_4$, and concentrated under reduced pressure to obtain 0.60 g (yield 34%) compound 81 as a yellow oil.

(3) Synthesis of Compound 82.1 and 82.2

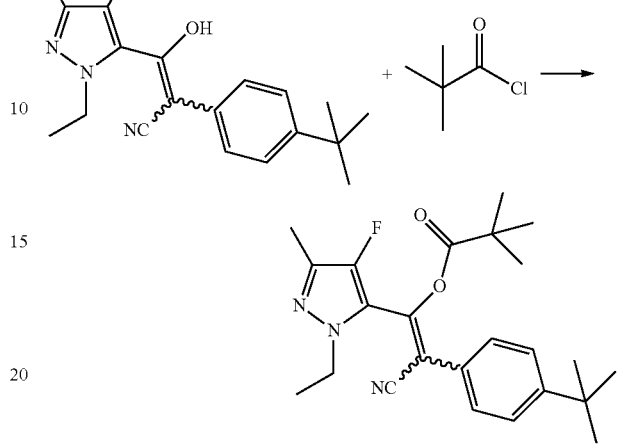

To the mixture of 3-(1-ethyl-4-fluoro-3-methylpyrazol-5-yl)-2-(4-tertbutylphenyl)-3-hydroxy-acrylonitrile (81) (0.50 g, 0.002 mol), triethylamine (0.30 g, 0.003 mol) in 10 mL of THF in the flask, pivaloyl chloride (0.35 g, 0.003 mol) was added dropwise in ice-water bath, then stirred at r.t. for 2 h. After removal of the solvent under reduced pressure, the residue was partitioned between 100 mL of ethyl acetate and 50 mL of water, the organic layer was washed with 100 mL of saturated aqueous sodium bicarbonate solution and 100 mL of saturated brine, dried over anhydrous MgSO$_4$ and concentrated. Column chromatography (EtOAc:P.E.=1:20 as eluent) gave the compound 82.1 (yellow oil, 0.09 g, yield 14%) and 82.2 (yellow oil, 0.16 g, yield 25%), respectively.

Example 5

Synthesis of Compound 86, 90.1, 90.2

(1) Synthesis of Compound 86

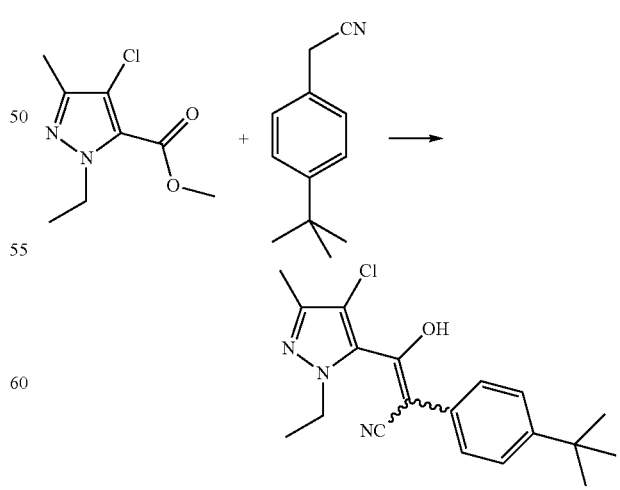

A mixture of methyl 4-chloro-1-ethyl-3-methylpyrazol-5-ylcarboxylate (2.57 g, 0.012 mol, Ref. CN1626520A), p-tertbutylphenylacetonitrile (1.85 g, 0.010 mol), ethylene glycol ethyl ether (3 mL) in heptane (30 mL) was stirred at room temperature under the atmosphere of nitrogen in the flask with Dean-Stark trap, then azeotropic dehydration was carried out under heating to reflux for 1 h. To the reaction mixture, 20% sodium methoxide methanol solution (3.17 g, 0.015 mol) was dropwised, and the resulting mixture was further reacted for 4 h under reflux. After cooling to 30° C., the resulting mixture was extracted with 100 mL of water and 100 mL of ethyl acetate. The aqueous layer was acidified to pH 2~3 by concentrated hydrochloric acid and extracted with ethyl acetate (3×100 mL). The organic layer was washed with 200 mL of saturated aqueous sodium bicarbonate solution and 200 mL of saturated brine, dried over anhydrous $MgSO_4$, and concentrated under reduced pressure to obtain 1.41 g (yield 38%) compound 86 as a yellow oil.

(2) Synthesis of Compound 90.1 and 90.2

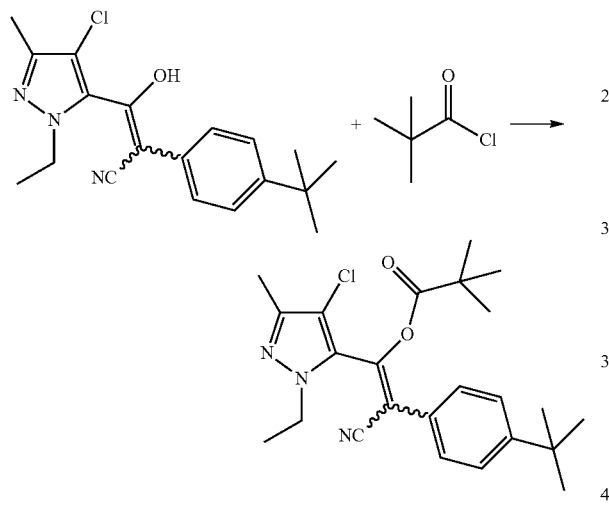

To the mixture of 3-(4-chloro-1-ethyl-3-methylpyrazol-5-yl)-2-(4-tertbutylphenyl)-3-hydroxy-acrylonitrile (86) (0.60 g, 0.002 mol), triethylamine (0.30 g, 0.002 mol) in 10 mL of THF in the flask, pivaloyl chloride (0.35 g, 0.003 mol) was added dropwise in ice-water bath, then stirred at r.t. for 1 h. After removal of the solvent under reduced pressure, the residue was partitioned between 100 mL of ethyl acetate and 50 mL of water, the organic layer was washed with 100 mL of saturated aqueous sodium bicarbonate solution and 100 mL of saturated brine, dried over anhydrous $MgSO_4$ and concentrated. Column chromatography (EtOAc:P.E.=1:20 as eluent) gave the compound 90.1 (white solid, 0.11 g, yield 15%, m.p. 93-94° C.) and 90.2 (white solid, 0.38 g, yield 51%, m.p. 124-125° C.), respectively.

The solution of compound 90.1 (0.1 g) dissolved in 5 mL of acetone, was slightly evaporated to obtain colourless crystal at r.t. The crystal was selected for the X-ray diffraction, which size was about 0.38 mm×0.34 mm×0.28 mm. The number of diffraction data amounts to 6437, and 4354 ($R_{int}$ 0.0149) are independent diffraction data. 4354 observable reflections (I>2σ(I)) were used to determine and refine structure. All calculation was implemented by the procedure of SHELXL-97 and afforded the deviation factor R 0.0388, wR 0.0935 and molecule structure of compound 90.1 at last.

The solution of compound 90.2 (0.1 g) dissolved in 5 mL of acetone, was slightly evaporated to obtain colourless crystal. The crystal was selected for the X-ray diffraction, which size was about 0.38 mm×0.32 mm×0.30 mm. The number of diffraction data amounts to 6269, and 4137 ($R_{int}$ 0.0162) are independent diffraction data. 4137 observable reflections (I>2σ(I)) were used to determine and refine structure. All calculation was implemented by the procedure of SHELXL-97 and afforded the deviation factor R 0.0331, wR 0.0838 and molecule structure of compound 90.2 at last.

Example 6

Synthesis of Compound 101.1, 101.2

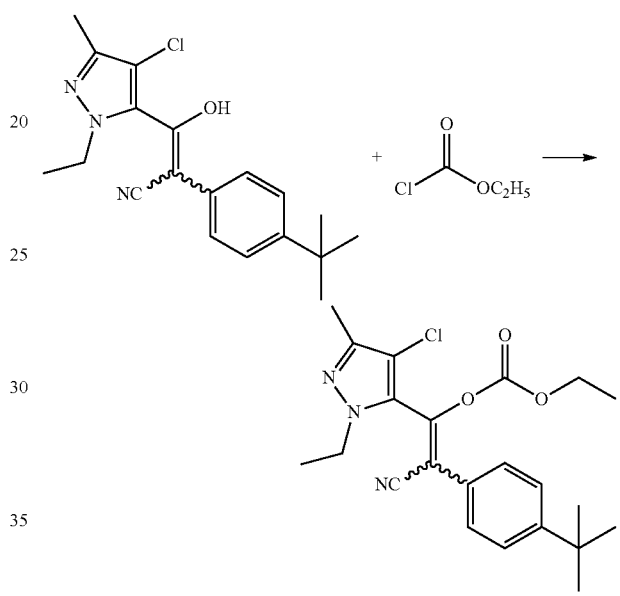

To the mixture of 3-(4-chloro-1-ethyl-3-methylpyrazol-5-yl)-2-(4-tertbutylphenyl)-3-hydroxy-acrylonitrile (86) (0.60 g, 0.002 mol), triethylamine (0.27 g, 0.003 mol) in 10 mL of dichloromethane in the flask, ethyl chloroacetate (0.32 g, 0.003 mol) was added dropwise at r.t. for 30 min. After removal of the solvent under reduced pressure, the residue was partitioned between 100 mL of ethyl acetate and 50 mL of water, the organic layer was washed with 100 mL of saturated aqueous sodium bicarbonate solution and 100 mL of saturated brine, dried over anhydrous $MgSO_4$ and concentrated. Column chromatography (EtOAc:P.E.=1:10 as eluent) gave the compound 101.1 (yellow oil, 0.11 g, yield 15%) and 101.2 (yellow oil, 0.24 g, yield 33%), respectively.

Example 7

Synthesis of Compound $KC_1$, $KC_2$

The compound $KC_1$ and $KC_2$ were synthesized as literature in JP2003201280A described. The solution of compound $KC_1$ (1 g) dissolved in 10 mL of acetone, was slightly evaporated to obtain colourless crystal. The crystal was selected for the X-ray diffraction, which size was about 0.38 mm×0.32 mm×0.30 mm. The number of diffraction data amounts to 12177, and 4174 ($R_{int}$ 0.0149) are independent diffraction data. 4174 observable reflections (I>2σ(I)) were used to determine structure and refine. All calculation was implemented by the procedure of SHELXL-97 and afforded the deviation factor R 0.0392, wR 0.1005 and molecule structure of compound KC, at last.

The solution of compound $KC_2$ (1 g) dissolved in 10 mL of acetone, was slightly evaporated to obtain colourless crystal. The crystal was selected for the X-ray diffraction, which size was about 0.34 mm×0.32 mm×0.28 mm. The number of diffraction data amounts to 12247, and 4212 ($R_{int}$ 0.0177) are independent diffraction data. 4212 observable reflections (I>2σ(I)) were used to determine structure and refine. All calculation was implemented by the procedure of SHELXL-97 and afforded the deviation factor R 0.0654, wR 0.1894 and molecule structure of compound $KC_2$ at last.

Example 8

Synthesis of Compound $KC_3$

The compound $KC_3$ was synthesized as literature in CN101367784A described, yellow oil.

$^1$H NMR (300 MHz, $CDCl_3$): 7.58 (d, 2H), 7.49 (d, 2H), 3.97 (s, 3H), 2.65 (q, 2H), 2.21 (s, 3H), 1.36 (s, 9H), 1.27 (t, 3H).

Biological Test

According to the solubility of test compounds, the compounds are dissolved in acetone or dimethyl sulfoxide, and then diluted with 0.1% aqueous solution of Tween 80 to form 50 ml test liquid, the content of acetone or dimethyl sulfoxide in the total solution is not more than 10%.

Example 9

Tests of Acaridical Activity (1) Test Against Adult Spider Mite (*Tetranychus cinnabarinus*)

The adult spider mites (*Tetranychus cinnabarinus*) were put into two true leaves of bean plants. After the number of mites were investigated, the solution of certain concentrations of test compounds was sprayed using a sprinkler and repeated three times. Then the leaves were maintained in standard observation room. After 72 h the survival mites in each leaf were observed, and mortality of the mites was determined.

According to above method, the representative compounds of this invention, compound KC, (compound 30 in JP2003201280A, E configuration), $KC_2$ (compound 31 in JP2003201280A, Z configuration) and $KC_3$ (compound 24 in CN101367784A) were chosen to parallel activity test against adult spider mites. Some test results were listed in Table 2.

TABLE 2

Acaricidal activity data against adult spider mites (mortality, %)

| compd. | concentration ppm | | | | |
|---|---|---|---|---|---|
| | 10 | 5 | 2.5 | 1.25 | 0.63 |
| | acaricidal activity | | | | |
| 5.1 | 100 | 100 | 100 | 98 | 42 |
| 5.2 | 100 | 100 | 87 | 65 | 56 |
| 6.1 | 100 | 100 | 100 | 100 | /* |
| 6.2 | 100 | 100 | 95 | 50 | / |
| 42.1 | 100 | 100 | 100 | 93 | 20 |
| 42.2 | 100 | 100 | 100 | 70 | 51 |
| 43.1 | 100 | 100 | 100 | 100 | / |
| 44.2 | 100 | 100 | 100 | 97 | 65 |

TABLE 2-continued

Acaricidal activity data against adult spider mites (mortality, %)

| compd. | concentration ppm | | | | |
|---|---|---|---|---|---|
| | 10 | 5 | 2.5 | 1.25 | 0.63 |
| | acaricidal activity | | | | |
| 50.1 | 100 | 100 | 100 | 100 | 93 |
| 54.1 | 100 | 100 | 100 | 100 | / |
| 90.1 | 100 | 100 | 100 | 100 | 55 |
| 90.2 | 100 | 100 | 100 | 100 | 28 |
| 91.1 | 100 | 100 | 100 | 90 | 74 |
| 91.2 | 100 | 100 | 98 | 60 | / |
| 101.1 | 100 | 100 | 91 | 50 | / |
| 102.2 | 100 | 100 | 100 | 30 | / |
| $KC_1$ | 100 | 100 | 85 | 30 | / |
| $KC_2$ | 100 | 100 | 55 | 0 | / |
| $KC_3$ | 5 | / | / | / | / |

*"/" stands for not tested.

(2) Test Against Deutonymph of Spider Mite (*Tetranychus cinnabarinus*)

Ten healthy female adult spider mites (*Tetranychus cinnabarinus*) were put into two true leaves of bean plants. The adult spider mites were removed after 24 h and the eggs were continued incubating. After ten days, the number of deutonymph were investigated and recorded. The solution of certain concentrations of test compounds was sprayed using a sprinkler and repeated three times. Then the deutonymph of spider mites were maintained in standard observation room. After 72 h, the survival mites in each leaf were observed, and mortality of the mites was determined.

According to above method, high acaricidal compound 5.1, 90.1 in present invention, and known high acaricidal compound $KC_1$ were chosen to parallel activity test against deutonymph of spider mite. The test results were listed in Table 3.

TABLE 3

Acaricidal activity data against deutonymph of spider mites (mortality, %)

| compd. | concentration ppm | | |
|---|---|---|---|
| | 2.5 | 0.63 | 0.16 |
| | acaricidal activity | | |
| 5.1 | 100 | 100 | 94 |
| 90.1 | 100 | 90 | 82 |
| $KC_1$ | 82 | 70 | 20 |

(3) Test Against Egg of Spider Mite (*Tetranychus cinnabarinus*)

Two true leaves of bean plants were taken and one true leaf was removed. Then ten healthy female adult spider mites were put into the true leaf. The adult spider mites were removed after 24 h and the eggs were investigated. The solution of certain concentrations of test compounds was sprayed using a sprinkler and repeated three times. The untreated eggs were all incubated after 5 days. The unincubation of treated eggs in leaf were observed, and incubation inhibition rate of the eggs were determined.

According to the above method, high acaricidal compound 5.1, 90.1 in present invention, and known high acaricidal compound $KC_1$ were chosen to parallel activity test against eggs of spider mites. The test results were listed in Table 4.

TABLE 4

Acaricidal activity data against eggs of spider mites (incubation inhibition rate, %)

| compd. | concentration ppm | | |
|---|---|---|---|
| | 10 | 5 | 2.5 |
| | acaricidal activity against eggs | | |
| 5.1 | 100 | 100 | 66 |
| 90.1 | 100 | 100 | 73 |
| $KC_1$ | 100 | 84 | 7 |

(4) Test of Systemic Activity Against Spider Mite Through Root Absorbtion

The test compounds are dissolved in acetone, and then diluted with 0.1% aqueous solution of Tween 80 to form test solution in different concentration and every treatment was repeated three times. Water is blank control. The 10 mL test compound solution was added into the tube. Two true leaves bean plants were taken and the soil in the root was removed. The bean plant was dipped into the test solution in different concentration. After absorbing 24 h, 30 to 50 spider mites were put onto the true leaves. Then the bean plants were maintained in observation room at 25±1° C. After 72 h, the death and survival mites in each leaf was observed, the mortality of the mites and systemic activity was determined. The test results were listed in Table 5.

TABLE 5

Comparsion on systemic activity against spider mites of compound 90.1 and compound $KC_1$ through root absorbtion (mortality, %)

| compd. | concentration ppm | | |
|---|---|---|---|
| | 200 | 100 | 50 |
| | acaricidal activity | | |
| 90.1 | 100 | 98 | 66 |
| $KC_1$ | 0 | 0 | 0 |

Example 10

Test Against Peach Aphid (*Myzus peisicae* Sulzer)

The cabbage leaves with peach aphids were taken and after the number of peach aphids were investigated, the solution of certain concentrations of test compounds was sprayed using a sprinkler and repeated three times. Then the leaves were maintained in standard observation room. After 72 h, the survival peach aphids were observed, and mortality of the peach aphids was determined.

The test of compound 81 at the concentration of 600 ppm showed 60% mortality against peach aphid.

What is claimed is:

1. A pyrazolyl acrylonitrile compound having formula I:

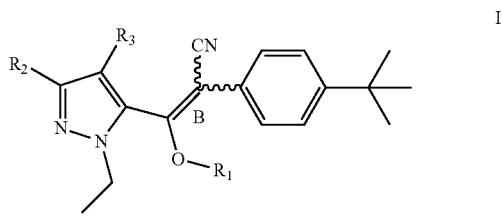

wherein:
$R_1$ is H, $C_1$-$C_4$ alkoxy $C_1$-$C_2$ alkyl, $C_3$-$C_5$ alkenyloxy $C_1$-$C_2$ alkyl, $C_3$-$C_5$ alkynyloxy $C_1$-$C_2$ alkyl, $C_1$-$C_4$ alkylthio $C_1$-$C_2$ alkyl, $C_1$-$C_5$ alkyl carbonyl, $C_3$-$C_8$ cycloalkyl carbonyl, $C_1$-$C_5$ alkoxy carbonyl, or $C_1$-$C_4$ alkylthio carbonyl;
$R_2$ is Cl or methyl;
$R_3$ is H, methyl, CN, $NO_2$, or halogen; or
a stereoisomer thereof.

2. The compound according to claim 1, wherein:
$R_1$ is H, $C_1$-$C_4$ alkoxy $C_1$-$C_2$ alkyl, $C_1$-$C_5$ alkyl carbonyl, $C_3$-$C_8$ cycloalkyl carbonyl, or $C_1$-$C_5$ alkoxy carbonyl;
$R_2$ is methyl;
$R_3$ is H, methyl, CN, or halogen; or
a stereoisomer thereof.

3. The compound according to claim 2, wherein:
$R_1$ is $C_1$-$C_2$ alkoxy methyl, $C_4$-$C_5$ alkylc arbonyl, $C_3$-$C_5$ cycloalkyl carbonyl, or $C_1$-$C_2$ alkoxy carbonyl;
$R_2$ is methyl;
$R_3$ is H, CN, F or Cl;
a stereoisomer thereof.

4. A method of controlling mites or insects, which comprises using a compound according to claim 1.

5. An insecticidal or acaricidal composition, comprising a compound according to claim 1 and and an acceptable carrier, wherein the amount of the compound is in the range of 1%-99% by weight of the composition.

6. A method for controlling insects or mites, applying the composition of claim 5 to the insects or mites or to the medium upon which the insects or mites grow, wherein the amount applied is an effective dosage within a range of 10 g/ha to 1000 g/ha.

* * * * *